United States Patent [19]

Ikeda et al.

[11] Patent Number: 4,925,743
[45] Date of Patent: May 15, 1990

[54] DISPOSABLE BODY WARMER AND HEAT GENERATING MATERIAL THEREFOR

[75] Inventors: Tamehiko Ikeda, Izumisano; Shusuke Yano, Akou, both of Japan

[73] Assignees: Nihon Food Culture Co., Ltd., Osaka; Tateho Chemical Industries Co., Ltd., Ako, both of Japan

[21] Appl. No.: 344,490

[22] Filed: Apr. 27, 1989

Related U.S. Application Data

[63] Continuation of Ser. No. 176,243, Mar. 31, 1988, abandoned.

[30] Foreign Application Priority Data

Mar. 31, 1987 [JP] Japan .................................. 62-80118
Mar. 25, 1988 [JP] Japan .................................. 63-72786

[51] Int. Cl.$^5$ ............................................... A61F 7/03
[52] U.S. Cl. ..................................... 428/702; 128/399
[58] Field of Search .................. 428/702; 128/399, 403

[56] References Cited

U.S. PATENT DOCUMENTS

| | | | |
|---|---|---|---|
| 3,202,801 | 8/1965 | Saluri | 128/399 X |
| 3,612,059 | 10/1971 | Ersek | 128/399 |
| 3,643,665 | 2/1972 | Caillouette | 128/403 |
| 4,114,591 | 9/1978 | Nakagawa | 128/403 X |
| 4,205,685 | 6/1980 | Yoshida et al. | 128/399 |

FOREIGN PATENT DOCUMENTS

| | | | |
|---|---|---|---|
| 2371503 | 7/1978 | France | 128/399 |
| 156841 | 12/1979 | Japan | 128/403 |
| 0024001 | 2/1980 | Japan | 128/399 |
| 0130660 | 10/1980 | Japan | 128/399 |
| 0001150 | 1/1981 | Japan | 128/399 |
| 0020450 | 2/1981 | Japan | 128/399 |
| 156840 | 7/1981 | Japan | 128/399 |
| 0130039 | 8/1983 | Japan | 128/403 |

*Primary Examiner*—Nancy A. B. Swisher
*Attorney, Agent, or Firm*—Jones, Tullar & Cooper

[57] ABSTRACT

A disposable body warmer comprises a heat generating material and a structure for retaining the material. The retaining structure may be provided on its one side with a reflecting material. The heat generating material consists essentially of at least one oxide of alkaline earth metals such as magnesium oxide with a plate crystal structure and, if necessary, contains an additive such as a salt selected from the group consisting of chlorides and sulphides of alkali metals and alkaline earth metals.

8 Claims, 3 Drawing Sheets

DISPOSABLE BODY WARMER AND HEAT GENERATING MATERIAL THEREFOR

This is a continuation of co-pending application Ser. No. 07/176,243 filed on Mar. 31, 1988, now abandoned.

FIELD OF THE INVENTION

This invention relates to a disposable body warmer and a heat-generating material therefor. More particularly, the present invention relates to a disposable body warmer which can be used even in summer and is suitable for medical use.

BACKGROUND OF THE INVENTION

So far, there have been known various disposable body warmers, or so-called "chemical body warmers" of the kind wherein heat is generated by exotheric reaction of chemical compounds. The commercially available disposable body warmers generally comprise a heat generating composition comprising powder of an easily oxidizable metal such as iron and an oxidizing agent, which are packed in a bag. In use, the metal powder and oxidizing agent are mixed with each other to allow the metal powder to react with the oxidizing agent, thereby generating heat. In such body warmers, the heat generating composition is generally added with additives to control the heat-generating characteristics including life and maximum temperature.

However, the chemical body warmers of the prior art are generally designed for winter use, so that the temperature of the body warmers rises to 40° C. and above at the lowest. Thus, if the body warmer is used for a long time as a hot compress for a patient in a hospital, there is a fear of thermal burn at a low temperature. In addition, because the transfer of heat from the chemical warmer depends on thermal conduction, the user can feel a warmth on his skin near the warmer, but cannot have a warmth to the bone.

On the other hand, with a recent widespread of air conditioning systems, there is an increasing harmful influence on the health of occupants who must work for a long time in air-conditioned spaces such as office buildings, automobiles, factory work areas and the like. Because preferences vary considerably from person to person, some persons are in need of body warmers even in summer. However, the chemical body warmers of the prior art cannot be used for this purpose since they are too hot to use in summer.

SUMMARY OF THE INVENTION

It is therefore an object of the present invention to provide a disposable body warmer which can be used for a long time without causing thermal burn at a low temperature.

Another object of the present invention is to provide a disposable body warmer which can be used even in summer without providing the user with a hot feeling.

Still another object of the present invention is to provide a heat generating material for disposable body warmers which generate heat moderately for a long time.

These objects are achieved by use of at least one oxide of alkaline earth metals as an essential component of a heat generating material.

The above and other objects, features and advantages of the present invention will be further apparent from the detailed description given hereinafter. It should be understood, however, that detailed description and specific examples, while indicating preferred embodiments of the invention, are given by way of illustration only, since various changes and modifications within the spirit and scope of the invention will become apparent to those skilled in the art from this description.

DESCRIPTION OF THE INVENTION

Figure 1:
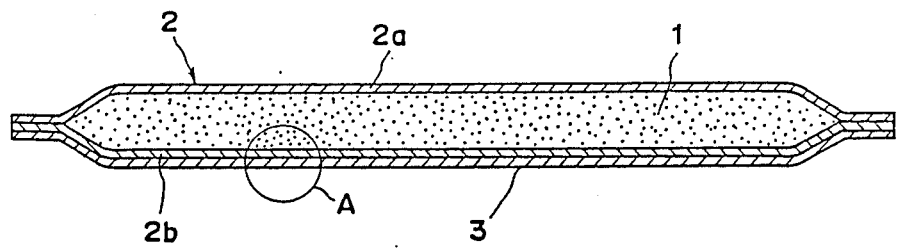
FIG. 1 is a cross section of a disposable body warmer showing one preferred embodiment of the present invention.

According to the present invention there is provided a heat generating material for disposable body warmers consisting essentially of at least one oxide of alkaline earth metals.

The alkaline earth metal oxides include, without being limited to, magnesium oxide and calcium oxide. Magnesium oxide includes low-temperature calcined magnesia, high-temperature calcined magnesia, and magnesium oxide with a plate crystal structure. These oxides may be used solely or in combination. If magnesium oxide is used solely as the heat generating material, it is preferred to use powder of magnesium oxide with a plate crystal structure having a garin size of 1 to 2 $\mu$m and a specific surface area of 10 m$^2$/g.

The heat generating material or composition of the present invention may contain, as an additive, at least one salt selected from the group consisting of chlorides and sulphides of alkali metals and those of alkaline earth metals. It is preferred to use a salt hydrate of the above compounds such as, for example, $MgCl_2 \cdot nH_2O$, $MgSO_4 \cdot nH_2O$ and the like. The above additive may be incorporated into the composition in an amount of up to 30% by weight.

According to the present invention there is further provided a disposable body warmer comprising a heat generating material and a means for retaining the material, the heat generating material consisting essentially of at least one oxide of alkaline earth metals.

The retaining means for the heat generating material may taken any desired shape. It is preferred to use the retaining means in the form of a sheet, film, bag, etc. As a material for the retaining means, there may be used those such as paper, nonwoven fabric, felt, and sheet or films of natural fibers, synthetic fibers or plastic resins.

In a preferred embodiment of the present invention, the disposable body warmer comprises a heat generating material consisting essentially of at least one oxide of alkaline earth metals; a means for retaining the material; and a reflecting means formed on one side of the retaining means.

The reflecting means may be formed by laminating or pasting a metal foil or a metallized film on the retaining means. The metallized film includes those prepared by depositing metal on a substrate. The substrate may be of paper, nonwoven fabric, felt, or clothes of natural fibers or synthetic fibers, or sheets of plastic films. The reflecting means may be formed directly on one side of the retaining means by the well known thin film technology such as vapor deposition, sputtering, printing, coating and like. As a material for reflecting means, there may be used those such as aluminum, nickel and other metals which make it possible to form a bright metal layer on the substrate.

In use, the alkaline earth metal oxide absorbs moisture present in the surroundings, thereby generating heat moderately. At the same time, because the alkaline earth metal oxide is heated by the heat of reaction or heat from the human body, it radiates far infrared rays. This effect is remarkable for magnesium oxide, especially, of a plate crystal structure since it has high emissivity at low temperature. Thus, the disposable body warmer of the present invention generates not only moderate heat but far infrared rays. When the disposable body warmer is applied to a human body in such a manner that one side of the warmer opposite to the reflecting means faces the skin, the far infrared rays radiated outwardly are reflected inwardly by the reflector, thus making it possible to minimize the loss of radiation. Also, because the far infrared rays penetrate into the skin, the user feels a warmth even if the warmer has a relatively low temperature approximately equal to body temperature, for example, about 38° C. or below.

Thus, there is no fear of thermal burns at a low temperature even if the disposable body warmer is used continuously for a long time. When the disposable body warmer of the present invention is placed in a temperature of about 20° C., its temperature rises to 30° C. at the highest, thus making it possible to use the warmer not only in winter season but in the summer season. Also, the disposable body warmer can be used as a hot compress for medical use. In addition, the heat-generating material of the present invention can be applied to clothing, bedclothes, footwear, wall members and the like.

Figure 2:
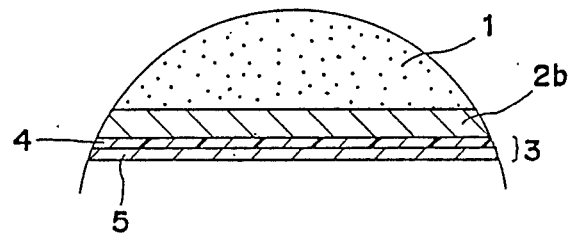
FIG. 2 is an enlarged cross section showing another of a disposable body warmer embodying the present invention.

Referring now to FIG. 1, there is shown a disposable body warmer embodying the present invention, which comprises a heat-generating composition 1 filled in a retaining bag 2. The bag 2 is provided on its one side $2a$ with a reflecting means 3. This reflecting means is provided by pasting a metal foil on the sheet material for the bag. In an embodiment shown in FIG. 2, the reflecting means 3 is formed by a metallized film laminated on the one side of a sheet $2b$ for the bag 2. The metallized film is composed of a thin metal layer 4 deposited on a substrate 5 by the well-known thin film technology such as vapor deposition, coating, printing, and the like.

Figure 3:
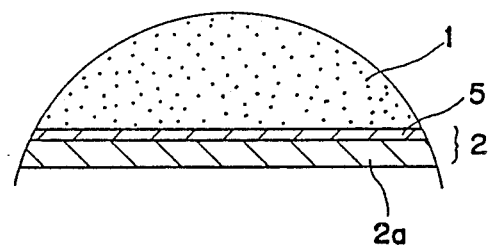
FIG. 3 is an enlarged cross section similar to FIG. 2 showing another embodiment of the present invention.

In the embodiment of FIG. 3, the reflecting means 3 is integrally formed on the inside of the bag 2. The bag may be prepared by combination of a nonwoven fabric and a laminated film with a thin metal layer as the internal layer. The metal layer may be formed by coating, printing, deposition, or the like.

Figure 4:
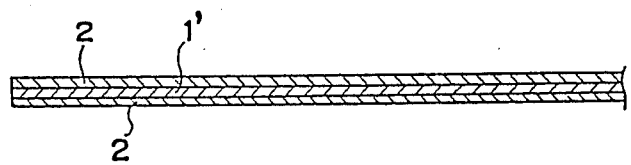
FIG. 4 is a cross section of a disposable body warmer showing still another embodiment of the present invention.

FIG. 4 shows another form of a disposable body warmer of the present invention, which comprises a heat generating layer $1'$ sandwiched between substrates 2. Such a disposable body warmer may be produced, for example, by extrusion laminating, thermocompresion bonding, extrusion coating, and the like. For example, the disposable body warmer is prepared by spreading a powder of the heat generating composition in a thin film on a substrate, and then extrusion coating a molten resin thereon. Instead of such a construction, the warmer may be composed of a substrate and a heat-generating layer containing a heat generating composition. The heat generating layer may be formed by adhering powder of the heat generating material to the substrate by a binder, or by applying a heat generating material dispersed in a molten resin to the substrate. In any case, it is preferred to form a reflecting layer on one side of the substrate.

EXAMPLE 1

Using nonwoven fabric of synthetic fibers as a material for substrate 2, there were prepared small bags 2 with a size of 9 cm×12 cm, and then an aluminum deposited film composed of polyethylene film and an aluminum layer deposited thereon was adhered to one side of the bag as a reflector 3. As a heat generating material, there was used powder of magnesium oxide with a plate crystal structure having a grain size of 1 to 2 $\mu$m and a specific surface area of 10 m$^2$/g. The bag was filled with 20 g of powder of magnesium oxide and then heat-sealed across its opening to complete a disposable body warmer as shown in FIG. 1.

The thus prepared disposable body warmer was placed in a room maintained at a temperature of 19.5° C. and a humidity of 60% to determine its temperature characteristics. The surface temperature of the disposable body warmer reached to 24° C. after 1 hour, and maintained that value even after 4 days.

Separate from the above, the disposable body warmer was contacted at its front side with a dried bean-curd with a 10 mm thickness containing 10% water and a temperature of the dried bean-curd was measured at the side opposite to the contacting surface. The surface temperature was raised to about 28° C. after 1 hour and kept at a temperature ranging from 28° to 30° C. even after 4 days.

From the above results, it will be seen that the disposable body warmer functions effectively under the presence of a small amount of moisture.

The disposable body warmers were distributed to twenty persons (ten males and ten females of not less than sixty years of age) and then applied to the abdomen or legs so that the front side $2a$ of the warmer is in contact with the skin, to determine how long the warmer would function. Results are shown in Table 1. The room temperature was 20° C. and the outside temperature was 2° C.

TABLE 1

| Time | number of persons | | |
|---|---|---|---|
| (min.) | warmish | warm | not warm |
| 60 | 3 | 17 | 0 |
| 120 | 2 | 18 | 0 |
| 180 | 5 | 15 | 0 |
| 240 | 5 | 15 | 0 |
| 300 | 12 | 8 | 0 |
| 360 | 13 | 7 | 0 |
| 420 | 14 | 6 | 0 |
| 480 | 15 | 5 | 0 |

All the persons reported that the warmth was felt slightly after about 10 minutes, but sharply after 30 minutes. It was also reported that the warmth was felt at the most about 120 minutes later. In addition, five persons who suffer from neuralgia have reported that the pain was abated. Also half of the persons have reported that the warmth was felt to the bone. Thus, the disposable body warmer of the present invention is superior in heat transfer to the disposable body warmers of the prior art. The results shown in Table 1 shows that the number of persons who feel the warmth decreases with the time. This results from the fact that the skin is enriched in the warmth.

EXAMPLE 2

Using the same nonwoven fabric and aluminum deposited film as those used in Example 1, small bags 2 of 4.5 cm×8.5 cm were prepared in the same manner as in Example 1. The bag was filled with 2g of plate crystal magnesium oxide having a grain size of 1 to 2 μm and a specific surface area of 10 m²/g and its opening then heat-sealed to complete a disposable body warmer.

The disposable body warmers were distributed to twenty females of not more than twenty-five years of age who work in an air-conditioned room kept at 20° C. and feel the cold at their feet. The warmers were so placed in shoes that the reflector side of the warmer comes into contact with the bottom of the shoes to determine to what extent they feel the warmth. Results are shown in Table 2.

TABLE 2

| Time | number of persons | | |
|---|---|---|---|
| (min.) | warmish | warm | not warm |
| 60 | 13 | 7 | 0 |
| 120 | 13 | 7 | 0 |
| 180 | 14 | 6 | 0 |
| 240 | 14 | 6 | 0 |
| 300 | 15 | 5 | 0 |
| 360 | 18 | 2 | 0 |
| 420 | 18 | 2 | 0 |
| 480 | 18 | 2 | 0 |

All the persons reported that the warmth was felt after 5 minutes and a comfortable, mellow warmth was maintained even after 8 hours although the warm decreased slightly after about 4 to 5 hours.

EXAMPLE 3

Powder of magnesium oxide was mixed with a polyethylene resin and then extrusion laminated on nonwoven fabric sheet by a T die to form a heat generating layer, which was then top covered by a nonwoven fabric sheet of rayon to sandwich the heat-generating layer between two sheets of the nonwoven fabrics, as shown in FIG. 4. The thus prepared laminate was provided on its one side with a commercially available aluminum deposited film, and then cut into square plates of 6 cm×6 cm to complete disposable body warmers. The content of magnesium oxide was 150 g per 1 m² of nonwoven fabric.

The thus prepared disposable body warmer was subjected to measurement of infrared radiation spectrum. The measurement was carried out under the following conditions:

Room temperature: 26° C.
Relative humidity: 55.0%
Specimen temperature: 135° C.

Figure 5:
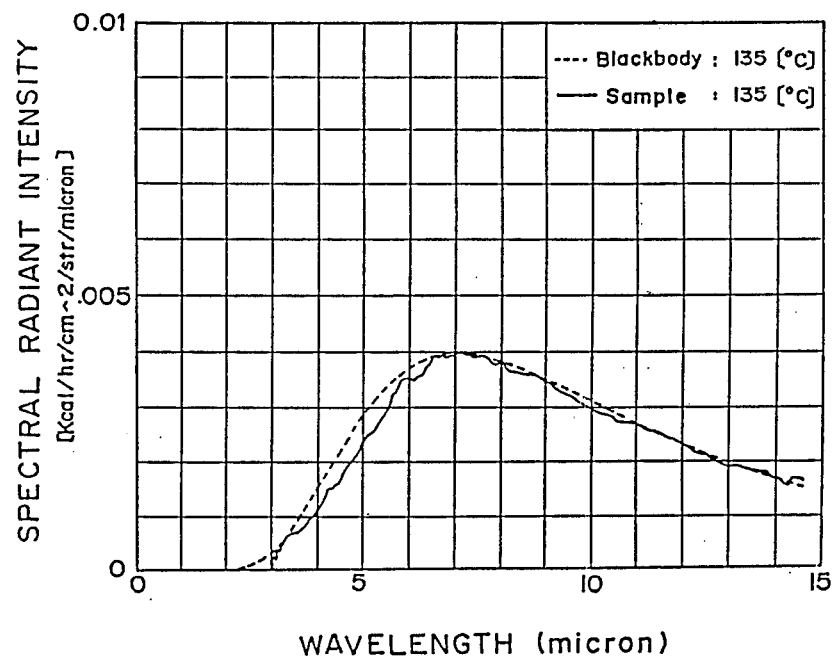
FIG. 5 is a graph showing spectral emission for a disposable body warmer of FIG. 4.

Results obtained are shown in FIG. 5. As can be seen from the results shown in FIG. 5, the disposable body warmer of the present invention has radiation characteristics close to that of a black body.

What is claimed is:

1. A disposable body warmer, comprising:
   a heat generating material for generating moderate heat and far infrared rays, consisting essentially of a powder of magnesium oxide with a plate crystal structure;
   retaining means for retaining said material so that it absorb moisture present in the surroundings; and
   reflecting means provided on one side of said retaining means to reflect far infrared rays radiated from said heat generating material.

2. A disposable body warmer according to claim 1, wherein said magnesium oxide powder has a grain size of 1 to 2 μm.

3. A disposable body warmer claimed in claim 1, wherein said retaining means is selected from the group consisting of paper, nonwoven fabric, felt, of nature fibers or synthetic fibers, and films of plastic resins.

4. A disposable body warmer claimed in claim 1, wherein said retaining means comprises two sheets of nonwoven fabric, and wherein said heat generating material in in the form of a layer and is sandwiched between said two sheets of nonwoven fabric.

5. A disposable body warmer claimed in claim 1, wherein said heat generating material is in the form of a layer and is sandwiched between said retaining means and said reflecting means.

6. A disposable body warmer claimed in claim 1, wherein said retaining means is formed in the form of a bag and contains said heat generating material therein.

7. A disposable body warmer claimed in claim 1, wherein said reflecting means is selected from the group consisting of metal foils, metallized films, and deposited metals.

8. A disposable body warmer comprising:
   a heat generating material for generating moderate heat and far infrared rays, consisting essentially of powder of magnesium oxide with a plate crystal structure and at least one additive selected from the group consisting essentially of chlorides and sulphides of alkali metals and alkaline earth metals;
   retaining means for retaining said material so that it absorbs moisture present in the surroundings; and
   reflecting means provided on one side of said retaining means to reflected far infrared rays radiated from said heat generating material.

* * * * *

UNITED STATES PATENT AND TRADEMARK OFFICE
CERTIFICATE OF CORRECTION

PATENT NO. : 4,925,743

DATED : May 15, 1990

INVENTOR(S) : Tamehiko Ikeda et al

It is certified that error appears in the above-identified patent and that said Letters Patent is hereby corrected as shown below:

Column 6

Claim 1, line 11, "essentially" should be deleted.

Claim 1, line 15, "absorb" should be "absorbs".

Claim 3, line 24, "clothes" should be inserted between the "," and "of", and "nature" should be "natural".

Claim 4, line 29, "in" (first occurrence) should be "is".

Claim 8, line 44, "essentially" should be deleted.

Claim 8, line 47, "essentially" should be deleted.

Claim 8, line 52, "reflected" should be "reflect".

Signed and Sealed this

Twenty-seventh Day of October, 1992

Attest:

DOUGLAS B. COMER

Attesting Officer      Acting Commissioner of Patents and Trademarks